United States Patent [19]

Fodor et al.

[11] Patent Number: 4,883,808

[45] Date of Patent: Nov. 28, 1989

[54] CONDENSATION PRODUCTS OF CYCLIC DIKETONES AND ASCORBIC ACID AS IMMUNOMODULATORY AGENTS

[75] Inventors: Gabor B. Fodor; Kawporn Sussangkarn, both of Morgantown, W. Va.; Robert W. Veltri, Gaithersburg, Md.

[73] Assignee: American Biotechnology Company, Rockville, Md.

[21] Appl. No.: 222,350

[22] Filed: Jul. 20, 1988

Related U.S. Application Data

[63] Continuation of Ser. No. 90,214, Aug. 27, 1987, abandoned.

[51] Int. Cl.$^4$ .................. A61K 31/365; C07D 493/14
[52] U.S. Cl. .................................... 514/468; 514/885; 549/298
[58] Field of Search ......................... 549/298; 514/468

[56] References Cited

FOREIGN PATENT DOCUMENTS 2104383  3/1983  United Kingdom ............... 549/298

Primary Examiner—John M. Ford
Attorney, Agent, or Firm—Wyatt, Gerber, Burke & Badie

[57] ABSTRACT

It has now been discovered that the acid catalyzed Michael reaction products of ascorbic acid and certain selected ketones are useful for their therapeutic activity. More specifically the useful reaction products of the invention are those obtained by reactions of ascorbic acid with $\alpha,\beta$ unsaturated alicyclic diketones containing from 5 to 7 carbon atoms.

The preferred compounds of the invention may be represented by the formula:

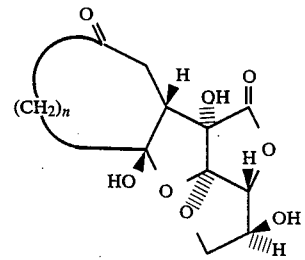

wherein n is 1, 2 or 3.

The ability of the compounds of this invention to stimulate an immune response has been established by a number of art recognized tests.

28 Claims, No Drawings

CONDENSATION PRODUCTS OF CYCLIC DIKETONES AND ASCORBIC ACID AS IMMUNOMODULATORY AGENTS

This application is a continuation of application Ser. No. 090,214, filed Aug. 27, 1987, now abandoned.

BACKGROUND OF THE INVENTION:

This application is concerned with Michael addition products of selected unsaturated aldehydes and ketones with ascorbic acid. It includes both L-ascorbic acid and its isomer D-ascorbic acid. L-ascorbic acid is also known as vitamin C. It is concerned also with pharmaceutical compositions containing the products as the principal active ingredients, and with methods of using the products for their physiological activity, especially to stimulate the immune response in animals and to treat infection of particularly viral infections such as those caused by retroviruses.

The compounds of this invention are useful as immunomodulating agents. They can be formulated with conventional pharmaceutical carriers for administration to animals and humans. The compounds and compositions containing them show immunomodulatory activity, especially immunostimulation at very low concentrations. As such they are useful for treatment of a wide variety of mammalian disorders which require stimulation of the immune system. These include, for example, stimulation of the immune system following chemotherapy or radiation therapy. The products are also useful to stimulate the proliferation of helper cells in diseases such as measles, retroviruses (HTLV-III), and leprosy which are characterized by an undesirably high concentration of suppressor cells. They are also useful in the early stages of various infections to stimulate the production of interleukins, interferons, and other atural lymphokines.

The immune system is one of the primary defenses against disease causing microbes and other foreign proteins in higher animals. An immune response is mediated by the action of specific antibody proteins which react to specific antigens. Antigens are substances of fairly high molecular weight, often proteins, which are foreign to an individual's body. They are most frequently located on the other surfaces of cells. Potential antigens can be found, for example, on pollen grains, tissue grafts, some tumor cell surfaces, animal parasites, viruses, and bacteria.

In humans, many potential antigens never pass the body's first two defense lines and therefore may not provide sufficient stimulation to the immune system. These two primary defense lines consist firstly of the skin, mucous membranes, tears, and stomach acid and secondly of specialized white blood cells, granulocytes and monocytes, and macrophages which may destroy pathogens and other potential antigens by phagocytosis, that is by engulfing and destroying the foreign material. These white blood cells and macrophages are called phagocytes. When pathogens or other foreign substances do pass the body's first two defense lines, the immune response begins.

There are two potential compartments of the immune defense system, humoral and cellular, both of which react to antigens. Humoral immunity is due to circulating antibodies which are found in the gamma globulin fraction of the plasma proteins. When plasma is centrifuged at high speed or chemically precipitated with ethanol by the Cohn procedure its component proteins separate by weight or charge into sections called fractions. Antibodies are usually found in the gamma globulin fraction whose components have a sedimentation constant of about 7-10S. The IgG fraction has a molecular weight of approximately 156,000. Humoral immunity provides long term protection against bacterial and viral infections. Cellular immunity is partly due to direct lympocyte interaction, or reactions with their products called lympocytes. This type of immunity is responsible for delayed allergic reactions, rejection of transplant of foreign tissue, and rejection of tumor cells. It is the major defense against infections due to viruses, fungi, parasites, and a few bacteria such as tubercle bacillus and plays a key role in recovery from such infections.

Specialized white blood cells called lymphocytes are responsible for both humoral and cellular immunity. The lymphocytes precursors originate as hematopoietic tissue ontogenetically (pre-natally) in the embryo before the appearance of bone. It is first evident in the yolk sac as "blood islands", small clusters of hematopoietic cells linked with the yolk blood vessels. These islands contain the multipotential hematopietic cells termed stem cells. As the embryo develops, hemopoietic cells invaginate into the body stock and into the mesenchymal bed in the anterior ventral portion of the abdomen contigous with the stalk. The liver migrates into this same site of the body mesenchyme as an evagination from the gut epithelium, proliferates, and assumes the architecture of hepatic cords among hemopoietic cells. The liver thereby becomes a hemopoietic organ until close to parturition. About half way through gestation the bone cavities begin to demonstrate definite hematopoietic tissue. As mammals approach embryonic maturity hematopoiesis recedes in the liver and the bone marrow becomes the dominant hematopoietic organ.

Post-natally the lymphoid organs of the body house the immunologically competent lymphocytes which characterize the immune system. The bone marrow houses the stem cells (precursor of all myeloid and lymphoid cellular elements). Some of these stem cells migrate to one of the primary lymphoid organs of man and other mammals, the thymus. The thymus is a multilobed organ that lies high behind the sternum. Here, the stem cells proliferate and differentiate into mature T-lymphocytes which then enter the circulation and seed secondary lymphoid organs including the spleen, lymph nodes, tonsils, appendix, and Peyer's patches in the gut. The bone marrow also seeds the gut-associated lymphoid system, distributed along the gut, with pre-B cells. These cells then proliferate and differentiate under the influence of antigenic stimulation and migrate to the same secondary lymphoid organs described above. The T-cells and B-cells are structurally and functionally distinguishable through various biological, immunochemical and biochemical means.

Humoral immunity is mediated by the B-lymphocytes which have immunoglobulin receptors for particular antigens on their cell surfaces. They seem to be very specific and each type of B-lymphocyte reacts to only one antigen. When bacteria or viruses, for example, invade an organism, B-lymphocytes react to and combine with the antigens on the bacterial or viral surface and the lymphocyte is stimulated to divide. Its daughter cells differentiate into specialized cells called plasma cells. These cells produce and then secrete large quantities of antibodies into the general circulation. The antibodies are specific for the antigens which stimulated their production and react only with those antigens. Antibodies formed in response to antigens by the plasma cells may be functionally differentiated as cytophilic, that is they are capable of combining with cellular antigens and enhancing phagocytosis by monocytes, macrophages and polymorphonuclear granulocytes in the peripheral circulation. Such antibodies may also be cytotoxic and on combination with cellular antigens in the presence of complement may cause lysis. Other antibodies may in the presence of specific antigen-sensitized T-cells produce antibody dependent cell lysis of tumor cells or virus infected cells. Antibodies produced to toxins or viruses may neutralize their toxicity or infectivity respectively by combining with the appropriate critical site for biological activity. Still other antibodies may be directed against the idiotypic determinant of an antibody molecule (the variable domain of the molecule), thereby being defined as an anti-idiotype or anti-antibodies (antibody 2) which are capable of regulating specific antibody synthesis or maintenance of antibody levels. IN the latter cascade, antibody may be formed to the anti-idiotype generating a new antibody (antibody 3) with a specificity to the original antigen. The latter may be achieved without the immunized animal ever having experienced challenge with the original antigen. Such technology may be of value in modifying the course of autoimmune or malignant diseases.

Once a pathogen invades the body and the immune response begins, antibodies are made between 10-14 days later. This initial reaction is called the primary response or primary immunization. However, during that time, the pathogens have also been dividing and producing various disease symptoms. It may take days or weeks before enough antibodies are made to eliminate all the pathogens but once they disappear, the disease symptoms disappear as well. The lymphocytes, plasma cells, and antibodies remain and circulate in the blood so that if the same pathogens enter the body a second time, the B-memory lymphocytes react immediately and start antibody production. The response of these pre-sensitized lymphocytes is called the secondary response. The secondary response results in the production of higher levels of antibody than were currently curculating in the plasma. So many antibodies are produced so rapidly that the microbes are unable to establish themselves, divide, and cause disease under the latter circumstances.

Humoral immunity produced by the IgE isotype of immunoglobulin has as one of its efferent reactions immediate hypersensitivity due to the fact that a previously exposed organism can respond within minutes to an antigen, as in the case of hay fever. Another example of immediate hypersensitivity would be anaphylactic shock, an extreme allergic reaction that sometimes occurs when an individual is exposed to an antigen to which he has been sensitized. Sometimes, this humoral response to the antigen can result in death.

Humoral immunity can also be both naturally and artificially induced. In the case of active natural acquired immunity, an individual's B-lymphocytes continue to circulate and activate the production of antibodies after an infection. This active natural acquired immunity lasts for many years or even a lifetime. An infant receives antibodies from the colostrum, milk secreted by the mother, the first few days after birth, which provides immunity during the first year of its life. This is known as passive natural immunity since the infant is not involved in the actual production of the antibodies. Active artificial immunity is induced by injecting dead or weakened (attenuated) microbes or synthetic antigens into an individual. These antigens can still trigger B-lymphocytes to produce antibodies against the causative pathogen. When the individual is later exposed to the virulent microbe, he is already sensitized and immediately responds with a massive secondary (memory) production of antibodies. Active artificial immunity may last many years or permanently with booster shots. There is also a form of passive artificial immunity which provides protection for about one month. This temporary immunity is brought about by injecting antibodies obtained from another person or animal into an individual. It is usually only used in crisis situations and epidemics. Because the lymphocytes are by passed, they neither make antibodies nor "remember" the antigen, which accounts for the temporary effect of this method.

In cellular immunity, as contrasted to humoral immunity, circulating antibodies are not detectable. The T-lymphocytes which mediate this type of immunity are activated when they encounter antigens on cells from another individual, as in the case of transplants, tumors, bacterial, or parasites or viruses. Like B-lymphocytes, T-lymphocytes are specific and each type reacts with only one antigen. The T-lymphocytes in the peripheral circulation are divided into subpopulations with different effector functions in the immune response. The T-helper inducer subpopulation has a specific receptor for antigen and is responsible for augmentation of the production of specific antibodies to the antigen by B-cells. The T-helper inducer is identified in humans by a surface marker referred to as the T-4 antigen and can be detected with monoclonal antibodies. Another key T-lymphocyte subpopulation is the T-suppressor inducer (T-8 antigen surface marker) lymphocyte which regulates the magnitude of response of certain T- and B-cells to specific antigens. There are also T-cytotoxic (killer) cells which can bind directly to target tumor or graft or virus infected cells causing their destruction. In addition when T-cells proliferate in response to antigen they produce lymphokines which participate in regulation of the immune response as well as removal of the foreign antigen. T-cells are directly involved in cell mediated immunity to tumor cells, virus-infected cells and other cellular antigens and clearly help in recovery from such disease processes. Also, the T-cells are responsible for allograft rejection, delayed, cutaneous hypersensitivity (DCH), chemical sensitization to poison ivy, oak, sumac as well as certain metals. This DCH reaction is called such because it takes 24-48 hours to develop subsequent to exposure to the antigen. Cellular immunity to new antigens usually occurs a few days before the primary (IgM) antibody response occurs in mammals and their are memory T-cells which are responsible for long term immunity. Another T-lymphocyte subpopulation is the natural killer (NK) T-cells (large granular lymphocytes) and these cells are called into action without prior antigenic provocation. These NK cells are active against tumors or virus infected cells and they can be stimulated to higher levels of activity (proliferation) by interferon. These cells are said to provide a key role in "immune surveillance" against cancer. T-cells as mentioned above, secrete lymphokines, a diverse and potent array of biologically active molecules with a variety of effects. Some select examples of these T-cell lymphokines include the interleukin 2 (T-cell growth factor), B-cell growth factor, interferon (gamma), and macrophages produce lymphokines (IL-1). These lymphokines serve at least two roles in the immune response, one is the regulation of immunity and the other is actual direct cytotoxicity (destruction) of tumor cells or virus-infected cells.

Immunomodulating agents activate or inhibit the process of lymphocyte proliferation. Normal lymphoctye proliferation is due to various interactions between antigens, macrophages, T- and B-lymphocytes. Additionally, certain B-lymphocytes can be activated by T-lymphocytes while others are independent of the T-lymphocytes and are activated only by antigens directly. Activated T-lymphocytes can cause macrophages to produce a molecule known as interleukin 2(IL-2) which in turn activates T-cells, which then stimulate other T- and B-lymphocytes. Activated macrophages can produce a molecule known as interleukin 1 (IL-1) which further induces T-lymphocyte activation. Chemicals, called mitogens can trigger DNA synthesis and mitosis which are signs of activity in T- and B-lymphocytes. Some mitogens affect only one type of lymphocyte while others affect many types. Immunomodulating agents of various kinds and in varying amounts affect the complex interactions between the components of the immune system. The compounds and compositions of this invention act as immune stimulators and affect both T-and B-lymphocytes.

The immune system has been linked to some aspects of aging and may be important in protecting against cancer. The system is necessary for the recognition of changing or aging cells, such as worn out red blood cells, and their subsequent destruction, and for this reason is vital to normal body functions. One theory in the case of cancer is that the transformation of cells to the malignant state may occur fairly frequently but these changed cells are recognized as "not self" and destroyed. Some carcinogens may work by depressing the immune response rather than by transforming cells themselves to a malignant state. This would mean that the body would no longer destroy the spontaneously transformed cells and a cancerous growth could escape, resulting in a tumor. Immunostimulation could be useful in treating such cancers.

Also, certain tumors which develop in man produce as a result of their growth an immunodepressed state in the hose (i.e. leukemias, lymphomas, respiratory cancers, and HTLV induced tumors).

Some of the methods of treating cancer, surgery, cytotoxic chemotherapy, and radiation for example, can result in a suppression or drastic variation of the normal functions of the immune system. Immunostimulatory drugs, such as the compounds and compositions of this invention can be very effective in combating and/or preventing various infections which can result due to the depressed immune system.

OBJECTS OF THE INVENTION

An object of the invention is to provide novel compounds having immunomodulatory activity, particularly immunostimulatory activity.

Another object of the invention is to provide methods for producing such compounds.

Another object of the invention is to provide novel compositions effective in the treatment of immune disorders, especially those requiring stimulation of the immune system.

Another object of the invention is to provide novel compounds and compositions useful for the treatment of virus infections in mammals, especially infections caused by retroviruses.

Other objects, advantages and novel features of the invention will become apparent from the following detailed description.

DESCRIPTION OF THE INVENTION

It has now been discovered that the acid catalyzed Michael reaction products of ascorbic acid and certain selected ketones are useful for their therapeutic activity. More specifically the useful reaction products of the invention are those obtained by reactions of ascorbic acid with α,β unsaturated alicyclic diketones containing from 5 to 7 carbon atoms.

The preferred compounds of the invention may be represented by the formula:

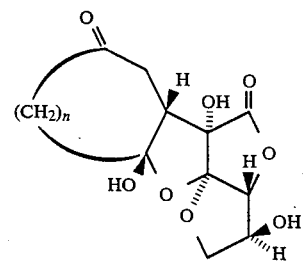

wherein n is 1, 2 or 3.

Typical compounds within the scope of this invention are represented by the following formulas.

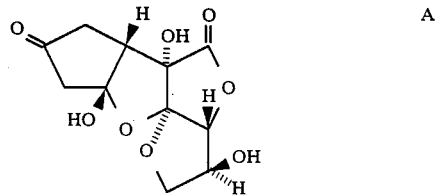

A

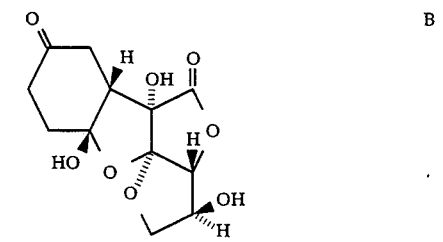

B

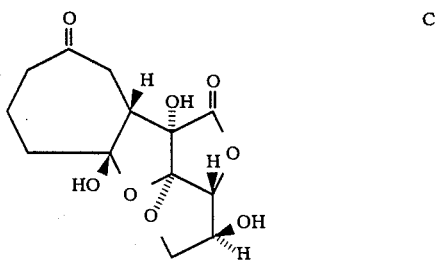

C

The chemical names for these compounds are, respectively

A. <3,3'>-hemiketal-<3,6>-ketal of 2-(1',3'-diketo-4'-cyclopentyl)-2-hydroxy-3-keto-4-dihydroxyethyl-butyrolactone B. <3,4'>-hemiketal-<3,6>-ketal of 2-(1',4'-diketo-3'-cyclohexyl)-2-hydroxy-3-keto-4-dihydroxyethyl-butyrolactone C. <3,3'>-hemiketal-<3,6>-ketal of 2-(1',4'-diketo-3'-cycloheptyl)-2-hydroxy-3-keto-4-dihydroxyethyl-butyrolactone These are the preferred compounds for use in the practice because the necessary starting compounds are readily available either commercially or by known methods of synthesis. The cyclohexyl compound is presently the most preferred because of its wide spectrum of physiological activity.

Those skilled in the art will recognize that several stereoisomers of the compounds of this invention may exist. The most obvious are those based on L- and D-ascorbic acid. However, as is known, further isomers of each of these isomers also exist, i.e., the 5- isoascorbic acids. So far as is known all isomers of the compounds of the invention have some activity, although certain of them are undoubtedly more active than others as is usually the case with naturally occurring physiologically active substance. As a practical matter, it is normally most convenient to synthesize the compounds of the invention without separation of stereoisomers and to utilize the stereoisomeric mixtures so produced. Applicant herein has followed the conventional practice in the specification and claims, i.e., unless specifically described or claimed the formulas employed include the stereoisomeric modifications.

The foregoing formulas all indicate that the compounds of this invention exist in tetracyclic form. This is because the presently available physical data indicates this to be the most stable form and the most probable form especially in the solid state. In solution the compounds most probably exist in equilibrium form as represented by the following equilibrium equations showing the compound prepared from 2-cyclohexene-1,4-dione.

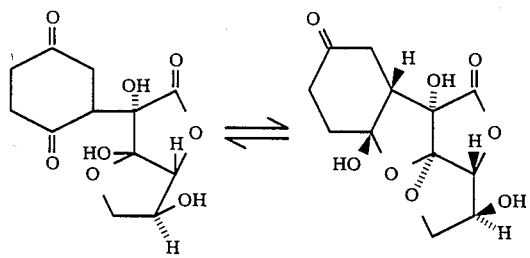

The left side formula in the above equilibrium equation illustrates more clearly than the tetracyclic formula on the right the possibility of position isomers based upon the positions of the ketones in the starting dione. For example, although 2-cyclohexene-1,4-dione is the preferred cyclohexene starting isomer because of its ready availability, the isomeric 3-cyclohexene-1,2-dione and 4-cyclohexene-1,3-dione can also be employed. Similar considerations also apply to the cyclopentene dione and cycloheptene dione.

The starting compounds used in this invention are available commercially or by known methods of synthesis. See, for example, Chapman et al J. Chem. Soc (C) 1969, 124 for the preparation of 2-cyclohexene-1,4-dione.

The reaction by which the compounds of this invention are prepared is carried out in an aqueous medium at ambient temperatures in the presence of a catalytic amount of a strong inorganic or organic acid, suitably a mineral acid such as sulfuric or a halogen acid, preferably hydrochloric acid. Preferably the reaction is conducted in an inert atmosphere such as nitrogen or helium.

The preferred reaction medium is water, although other solvents may be added, especially water miscible solvents such as lower alkanols, typically methanol, ethanol, or cyclic ethers such as tetrahydrofuran, or ketones particularly acetone. These will assist in dissolving some of the higher molecular weight, or hydrophobic reactants.

Reaction is effected at a temperature of from about 20° C. to 45° C. for a period of from about 2 to 48 hours. The reaction period is not critical. It depends principally on the quantities of the reactants. The reaction is readily followed by conventional analytical methods to determine when the reaction is complete, or when continued reaction is not warranted by expected increase in yield. High performance liquid chromatography is a convenient tool.

Generally equimolar quantities of the reactants will be employed. However, in certain instances it may be desirable to use a molar excess, e.g., up to about a 10% molar excess of one of the reactants to assure as complete a reaction as possible.

As aforesaid, any of a variety of strong acids can be employed to catalyze the reaction. Typically 0.1% to 1.5% by weight of acid based on the total weight of reactants will be employed. In an aqueous medium, hydrochloric acid is preferred since it is readily removed by precipitation as a chloride salt. However, a stronger carboxylic acid such as trichloroacetic acid or trifluoroacetic acid may be used.

It is surprising to find a Michael addition reaction catalyzed by acid. Usually this type of reaction which is an addition of an active methylene compound to an activated unsaturated system is catalyzed by base.

The ability of the compounds of this invention to stimulate an immune response has been established by a number of art recognized tests.

One of these tests is the lymphocyte blastogenesis assay which measures the ability of the compound under test to affect DNA synthesis and mitosis of T- and B- lymphocytes isolated from mouse spleens.

Mitogens are substances which stimulate DNA synthesis and mitosis. The mitogens used in these studies were phytohemaglutinin (PHA) which is isolated from the red kidney bean and a lipopolysacharide isolated from *Salmonella tythimurium* (LPS).

The lymphocyte blastogenesis test is a method to assess the ability of immunocompetent T- or B-cells to respond to mitogens or a specific antigen. It may be performed on lymphocytes obtained from mice treated with immunostimulators in vivo or the entire assay can be performed in vitro. The assay as described below uses minimal doses of polyclonal mitogens to induce blastogenesis (proliferation measured by DNA synthesis), in order to be able to assess the phenomena of amplification. Hence, the procedure is designed to test the ability of potential immunomodulators to restore normal immunologic parameters.

The lymphocyte blastogenesis test is carried out as follows:

1. Sacrifice two mice/experimental group by cervical dislocation.
2. Immerse mice in a mild disinfectant solution (Povadyne).
3. Remove spleens and place in a sterile 6 well plate containing 5 ml/well of RPMI-1640.
4. Make a single cell suspension by mincing spleens with a sterile toothed forcep.
5. Place cell suspension in a sterile centrifuge tube and allow large clumps to settle for 10 minutes.
6. Remove single cell suspension by pipetting supernatant into another sterile centrifuge tube.
7. Centrifuge cell suspension for 10 mins. at 1100 RPM in GLC-2B.
8. Aseptically remove supernatant and discard.
9. Resuspend cell button in 5 mls of RPMI-1640, and centrifuge. Wash cells in this manner two more times.
10. Resuspend cells in 5 mls of RPMI-1640 containing 10-15% Human AB heat-inactivated (Pel-Freeze, Rogers, AR or BioBee, Boston, MA).
11. Perform viable cell count using 0.25% trypan blue exclusion dye made in physiological isotonic saline. Non-viable cells stain blue.
12. Adjust viable cell concentration to $5.0 \times 10\text{-}6$ cells/ml in RPMI-1640 containing human AB sera.
13. Aliquot in sextuplicate wells of a 96 well sterile round bottom tissue culture plate with 0.1 ml/well of the various cell suspensions to be tested.
14. Add to above replicate sextuplicate cells selected quantities of mitogen.
15. Include in the experiment a control plate which contains the same cell groups as above, but receive a 0.1 ml of media instead of mitogen.
16. Humidify plate by filling outside wells of plate with media.
17. Incubate plates at 3 C. with 5% CO-2 for 48 hours.
18. After 48 hours all wells receive 0.025 mls of a 0.4 microcurie/ml solution of C-14 methyl thymidine and incubate at 37 C, 5% CO-2 for 18 hours.
19. The cells are harvested using a Brandel M-12 Cell Harvestor (Brandel, Rockfille, MD) onto filter paper discs using phosphate buffered saline at physiological osmolarity. (285-320 mos).
20. The filter paper disks are placed into Packard mini-scintillation vials and allowed to dry for 18 hours.
21. Once dried, the vials are filled with 2 mls of a scintillation cocktail containing 4 liters of scintillation grade toluene, 16.0 g of 2,5-diphenyloxazole (PPO) and 0.4 g of 1,4-Bis (2-(5-Phenyloxazoly) benzene (POPOP).
22. The vials are counted in a LKB 1212 Rackbeta (LKB Instruments, Gaithersburg, MD) Liquid scintillation counter for two minutes/vial.

The following table show the results of the lymphocyte blastogenesis assay of Compound B.

The compound of this invention has been found to exhibit antiviral activity, particularly against retroviruses.

The retroviruses are a broad group of RNA viruses which during their replication employ the reverse transcription enzyme (RT) to convert an RNA message to DNA. The retroviridae family of viruses includes Lentiviruses (visna, maedi, progressive pneumonia viruses—"slow viruses"), Spumaviruses (foamy viruses) and Oncornaviruses (types A, B, C, D, RNA tumor viruses). The retroviruses have been shown to infect murine, avian, feline, primate, and human species.

The human immunodeficiency virus (HIV) or human T-cell lymphotorpic virus (HTLV-III) which cause Acquired Immune Deficiency Syndrome (AIDS) and AID related complex (ARC) and AIDS related diseases is a retrovirus. Also the feline leukemia virus (FeLV) of cats is a retrovirus.

The virus rating (VR) of Compound A of this invention when tested in accordance with the method of Sidewell and Huffman (Appl. Microbiol. 22:795-801, 1971) against adenovirus type 2 utilizing HEp-2 as the target cell was greater than 0.2. The $ID_{50}$ (concentration in $\mu g./ml$ of the drug that causes 50% reduction in virus replication) was 505.19 $\mu g/ml$. The minimum toxic concentration (MTC) was greater than 320 $\mu g/ml$.

The same compound was also tested against feline leukemia virus by the Sidewell and Huffman procedure using the 81C cell line as the target. The 81C cell is a feline kidney cell transformed with a murine leukemia virus (ras gene +) with the following results.

| | |
|---|---|
| VR | 1.1 (control 0.98) |
| $ID_{50}$ | 4.5 |
| MTC | 100 |

The therapeutic index of the compound which is a measure of the compounds ability to protect the cell against the virus without adversely affecting cell growth was 22.

The antiviral activity of the compounds of this invention appears to be a two pronged attack. There is direct antiviral activity as with conventional antiviral agents. There is also the added factor of immunostimulation to marshal the bodies natural defenses against viruses or any other foreign agent.

The biologically active compounds of this invention may be administered in effective amounts alone or in combination with acceptable pharmaceutical carriers, the choice of which is determined by the preferred route of administration, the solubility of the compound and standard pharmaceutical practice. For oral administration, the compounds may be administered in the form of tablets containing excipients such as buffers, starch or

TABLE
EFFECT OF COMPOUND B ON THE LYMPHOCYTE BLASTOGENESIS ASSAY

| DRUG MG/KG | RPMI | PHA 10.0 UG/KG | % CHANGE | LPS 5.0 MG/KG | % CHANGE |
|---|---|---|---|---|---|
| 0 | 962 ± 431 | 7410 ± 88 | | 7039 ± 81 | |
| 200 | 660 ± 354 | 8111 ± 896 | +9.4 | 8025 ± 1670 | +14 |
| 100 | 705 ± 314 | 9258 ± 1391 | +24.9 | 8423 ± 351 | +19.6 |
| 50 | 1041 ± 687 | 10218 ± 2630 | +37.9 | 6823 ± 1305 | — |
| 25 | 1392 ± 247 | 7563 ± 2053 | +2.1 | 8580 ± 507 | +21.9 |
| 12.5 | 605 ± 117 | 7126 ± 1104 | −3.8 | 7195 ± 90 | +2.2 | milk sugar. Aqueous solutions and elixirs which may be buffered and sweetened or flavored may also be used. For intra-articular injection aqueous suspensions may be employed. In this case various suspending and wetting agents may be added to the composition to obtain a suspension not tending to settle out easily or to pack down in the bottle in which it is stored. Intramuscular and subcutaneous dosage forms may be prepared by standard pharmaceutical practice.

The compounds may be used in association with other therapeutic agents including, for example, antibiotics or antiviral agents. I may also be useful to employ the synthetic immunostimulators in association with natural immunostimulators such as interleukin 1 and 2, or interferon or it's synthetic inducers (i.e. poly IC-LC etc.), B-cell growth factors, or tumor necrosis factor. The resulting compositions may be administered by any of the usual routes of administration including intramuscular or intravenous.

The physician or veterinarian in attendance with determine the optimum dosage in consideration of such factors as age, weight and general health of the subject. A dose which will be effective to stimulate an immunomodulatory response will normally be from about 100 to 50 mg/kg body weight, although wide variations are possible. The dosage may be administered in one treatment or in several treatments given over a period of time.

The compositions of the invention may be made available in dosage unit forms typically containing a therapeutically effective amount of active ingredient per dosage unit.

The following examples are given solely for the purpose of illustration and are not to be construed as limitations of this invention, many apparent variations of which are possible without departing from the spirit or scope thereof.

EXAMPLE 1

<3,4'>-hemiketal-<3,6-ketal> of 2-(1',4'-diketo-3'-cyclohexyl)-2-hydroxy-3-keto-4-dihydroxyethylbutyrolactone Distilled water (82.5 mL) was purged for 1 hour with nitrogen and L-ascorbic acid (Mallinckrodt USP Grade) (20.94 g, 0.12 mole) was added. To the resulting solution 2-cyclohexene1,4-dione (13.09 g, 0.12 mole) was added portionwise with stirring. One half hour after the addition of the cyclohexenedione, 0.3 mL concentrated hydrochloric acid was added. The solution was allowed to stand undisturbed at room temperature for 24 hours when the formation of powdery solid was observed. The reactionmixture was cooled in ice-water bath and filtered by suction to give 5.65 g (17%) of an off-white powder. Two grams of the solid were recrystallized in 120 mL of hot 2:1 ethyl acetate:methanol to give 0.72 g of a white crystalline solid that shows a single peak in HPLC analysis (MCH 10 column with 80% water/methanol as eluent and 1.0 mL/min flow rate) with a retention time of 2.9 minutes, mp 198°–200° C., $[\alpha]_D^{27} = +2.7°$ (c=2.0, methanol).

EXAMPLE 2

Tablet Formulation

| Formula | Mg/tablet |
|---|---|
| COMPOUND B | 200.00 |
| Citric acid | 1.00 |
| Lactose | 33.00 |
| Diacalcium phosphate | 70.00 |
| Pluronic, F-68 | 30.00 |
| Sodium Lauryl Sulfate | 15.00 |
| Polyvinylpyrrolidone | 15.00 |
| Carbowax 1500 | 5.00 |
| 3A alcohol 50 ml./1000 tablets | |
| Corn Starch | 30.00 |
| Dry | |
| Sodium Lauryl Sulfate | 3.00 |
| Magnesium stearate | 3.00 |
| TOTAL WEIGHT | 350.00 |

Procedure

Mix together the Compound B, citric acid, Pluronic F-68, sodium lauryl sulfate, lactose and dicalcium phosphate. Screen through No. 60 mesh screen. Granulate the screened mix with an alcoholic solution containing the polyvinylpyrrolidone, Carbowax 1500 and 6000. Add additional alcohol, if necessary, to bring powder mix to a pasty mass. Add corn starch and continue mixing until uniform dam granules are formed. Pass the damp granulation through a No. 10 screen and dry in an oven at 100° C. for 12–14 hours. Screen the dried granulation using a No. 16 screen, add sodium lauryl sulfate and magnesium stearate, mix and compress on a tablet machine to specifications.

EXAMPLE 3

Capsule Formulation

| Formula | mg/capsule |
|---|---|
| Compound B | 100.00 |
| Citric acid | 1.00 |
| Pluronic F-68 | 40.0 |
| Sodium lauryl sulfate | 20.00 |
| Lactose | 238.00 |
| Magnesium stearate | 1.00 |

Procedure. Mix together the Compound B, citric acid, Pluronic F-68, sodium lauryl sulfate and lactose. Pass through a No. 80 screen. Add the magnesium stearate, mix and encapsulate into the proper size 2-piece gelatin capsule.

EXAMPLE 4

Parenteral Formulation

| Formula | | |
|---|---|---|
| COMPOUND B | mg/10 ml | 200 |
| Benzyl alcohol, UF | mg/10 ml | 50.0 |
| Methyl paraben, USP | mg/10 ml | 18.0 |
| Propyl paraben, USP | mg/10 ml | 2.0 |
| Water | ml | 10 |

Procedure.

Dissolve the parabens in approximately 8.5 ml of water at 60° to 70° C. Cool the solution at 40° C. and add the benzyl alcohol. Cool the resultant solution to room temperature and add the KCBL. Place the suspension in a sterile receptacle. Fill suitably sized vials cap loosely and autoclave for one-half hour at 110° C. (15 P.S.I.G.). Each milliliter of this formulation delivers 20 mgs. of active compound.

What is claimed is:

1. A compound of the formula:

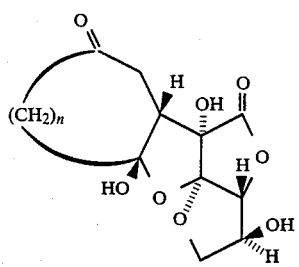

wherein n is 1, 2 or 3.

2. <3,3'>-hemiketal-<3,6>-ketal of 2-(1',3'-diketo-4'-cyclopentyl)-2-hydroxy-3-keto-4-dihydroxyethylbutyrolactone.

3. <3,4'>-hemiketal-<3,6>-ketal of 2-(1',4'-diketo-3'-cyclohexyl)-2-hydroxy-3-keto-4-dihydroxyethylbutyrolactone.

4. <3,4'>-hemiketal-<3,6>-ketal of 2-(1',4'-diketo-3'-cycloheptyl)-2-hydroxy-3-keto-4-dihydroxyethylbutyrolactone.

5. A pharmaceutical composition containing a pharmaceutically acceptable carrier together with the <3,3'>-hemiketal-<3,6>-ketal of 2-(1',3'diketo-4'-cyclopentyl)-2-hydroxy-3-keto-4-dihydroxyethylbutyrolactone.

6. A pharmaceutical composition containing a pharmaceutically acceptable carrier together with the <3,4'>-hemiketal-<3,6>-ketal of 2-(1',4'-diketo-3'-cyclohexyl)-2-hydroxy-3-keto-4-dihydroxyethylbutyrolactone.

7. A pharmaceutical composition containing a pharmaceutically acceptable carrier together with <3,4'>-hemiketal-<3,6>-ketal of 2-(1',4'-diketo-3'-cycloheptyl)-2-hydroxy-3-keto-4-dihydroxyethylbutyrolactone.

8. A method of stimulating the immune response of a mammal in need of such stimulation which comprises administering an amount which is effective to stimulate such response of <3,3'>-hemiketal-<3,6>-ketal of 2-(1',3'diketo-4'-cyclopentyl)-2-hydroxy-3-keto-4-dihydroxyethylbutyrolactone.

9. The method of claim 8 wherein the mammal is a human.

10. The method of claim 8 wherein the mammal is an animal.

11. A method of stimulating the immune response of a mammal in need of such stimulation which comprises administering an amount which is effective to stimulate such response of <3,4'>-hemiketal-<3,6>-ketal of 2-(1',4'-diketo-3'-cyclohexyl)-2-hydroxy-3-keto-4-dihydroxyethylbutyrolactone.

12. The method of claim 11 wherein the mammal is a human.

13. The method of claim 1 wherein the mammmal is an animal.

14. A method of stimulating the immune response of a mammal in need of such stimulation which comprises administering an amount which is effective to stimulate such response of <3,4'>-hemiketal-<3,6>-ketal of 2-(1',4'-diketo-3'-cycloheptyl)-2-hydroxy-3-keto-4-dihydroxyethylbutyrolactone.

15. The method of claim 14 wherein the mammal is a human.

16. The method of claim 14 wherein the mammal is an animal.

17. A pharmaceutical composition in dosage unit form containing a pharamceutically acceptable carrier together with <3,3'>-hemiketal-<3,6>-ketal of 2-(1',3'-diketo-4'-cyclopentyl)-2-hydroxy-3-keto-4-dihydroxyethylbutyrolactone.

18. A pharmaceutical composition in dosage unit form containing a pharmaceutically acceptable carrier together with <3,4'>-hemiketal-<3,6>-ketal of 2-(1',4'-diketo-3'-cyclohexyl)-2-hydroxy-3-keto-4-dihydroxyethylbutyrolactone.

19. A pharmaceutical composition in dosage unit form containing a pharmaceutically acceptable carrier together with <3,4'>-hemiketal-<3,6>-ketal of 2-(1',4'-diketo-3'-cycloheptyl)-2-hydroxy-3-keto-4-dihydroxyethylbutyrolactone.

20. A method of inhibiting retroviral activity of a mammal in need of such inhibition which comprises administering an amount which is effective to effect such inhibition of <3,3'>-hemiketal-<3,6>-ketal of 2-(1',3'diketo-4'-cyclopentyl)-2-hydroxy-3-keto-4-dihydroxyethylbutyrolactone.

21. The method of claim 20 wherein the mammal is a human.

22. The method of claim 20 wherein the mammal is an animal.

23. A method of stimulating the immune response of a mammal in need of such stimulation which comprises administering an amount which is effective to stimulate such response of <3,4'>-hemiketal-<3,6>-ketal of 2-(1',4'diketo-3'-cyclohexyl)-2-hydroxy-3-keto-4-dihydroxyethylbutyrolactone.

24. The method of claim 23 wherein the mammal is a human.

25. The method of claim 23 wherein the mammal is an animal.

26. A method of inhibiting retroviral activity of a mammal in need of such inhibition which comprises administering an amount which is effective to effect such inhibition of <3,4'>-hemiketal-<3,6>-ketal of 2-(1',4'diketo-3'-cyclopentyl)-2-hydroxy-3-keto-4-dihydroxyethylbutyrolactone.

27. The method of claim 26 wherein the mammal is a human.

28. The method of claim 26 wherein the mammal is an animal.

* * * * *